(12) United States Patent
Chan et al.

(10) Patent No.: US 10,702,139 B2
(45) Date of Patent: Jul. 7, 2020

(54) LARYNGOSCOPE WITH ROTATABLE AND TURNABLE DISPLAY

(71) Applicants: IEI INTEGRATION CORP., New Taipei (TW); ARMORLINK SH CORP., Shanghai (CN)

(72) Inventors: Kai-Cheng Chan, New Taipei (TW); Chin-Chia Chang, New Taipei (TW)

(73) Assignees: IEI Intergration Corp., New Taipei (TW); Armorlink SH Corp., Shanghai (CN)

( * ) Notice: Subject to any disclaimer, the term of this patent is extended or adjusted under 35 U.S.C. 154(b) by 435 days.

(21) Appl. No.: 15/412,402

(22) Filed: Jan. 23, 2017

(65) Prior Publication Data

US 2018/0206705 A1 Jul. 26, 2018

(51) Int. Cl.
*A61B 1/267* (2006.01)
*A61B 1/00* (2006.01)

(52) U.S. Cl.
CPC .......... *A61B 1/267* (2013.01); *A61B 1/00048* (2013.01); *A61B 1/00052* (2013.01)

(58) Field of Classification Search
CPC ... A61B 1/267; A61B 1/2676; A61B 17/0218; A61B 17/02; Y10T 403/7005; Y10T 403/7007; Y10T 403/60; Y10T 403/602; Y10T 403/604; Y10T 403/32508; Y10T 403/32524; Y10T 403/7079
USPC ................................................ 600/184–199
See application file for complete search history.

(56) References Cited

U.S. PATENT DOCUMENTS

| | | | | |
|---|---|---|---|---|
| 2,448,548 A | * | 9/1948 | Purdy | F16B 7/20 403/341 |
| 2003/0215283 A1 | * | 11/2003 | Hsieh | F16B 7/105 403/109.2 |
| 2004/0184876 A1 | * | 9/2004 | Hessel | A61F 5/448 403/326 |
| 2008/0146878 A1 | * | 6/2008 | Frost | A61B 1/00105 600/188 |
| 2009/0208281 A1 | * | 8/2009 | Noh | B60T 11/046 403/349 |
| 2011/0020059 A1 | * | 1/2011 | Yin | G01R 1/06722 403/326 |
| 2011/0110709 A1 | * | 5/2011 | Charuel | F16B 21/065 403/109.2 |
| 2012/0316398 A1 | * | 12/2012 | Ashcraft | A61B 1/267 600/188 |
| 2018/0071473 A1 | * | 3/2018 | Ferrario | A61B 1/00066 |

* cited by examiner

*Primary Examiner* — Amy R Sipp
(74) *Attorney, Agent, or Firm* — Rosenberg, Klein & Lee

(57) ABSTRACT

A laryngoscope with a rotatable and turnable display is revealed. The laryngoscope includes a laryngoscope body, a rotating assembly, a turnover assembly and a display. The laryngoscope body is used to capture images. The rotating assembly is disposed over the laryngoscope body and having a plurality of elastic bodies or first and second magnetic parts used in combination with a slot of a first fixed shaft. Thus the display is rotated around the rotating assembly and a rotation angle of the display is determined according to the position of the slot. The turnover assembly is arranged at one side of the display. The display is flipped around the turnover assembly by a fixing member of a second fixed shaft being mounted into at least one fixing hole of a turnover portion. The angle of the display being turned is determined according to the position of the fixing hole.

9 Claims, 14 Drawing Sheets

LARYNGOSCOPE WITH ROTATABLE AND TURNABLE DISPLAY

BACKGROUND OF THE INVENTION

Field of the Invention

The present invention relates to a laryngoscope, especially to a laryngoscope with a rotatable and turnable display.

Descriptions of Related Art

In order to deliver oxygen to patients with serious conditions or under full body anesthesia, medical staff needs to place a plastic endotracheal tube into patient's trachea, allowing patient to breath.

Generally, experienced doctors can open about 80% patient's mouse for tracheal intubation by a common laryngoscope. Yet for about 20% patients, doctors have difficulty in viewing the trachea opening directly owing to shorter jaw, harder neck or shorter neck. Thus a camera lens is disposed on a front end of the laryngoscope and is connected to a big screen by wires for observing images captured by the camera lens of the laryngoscope. However, the big screen is heavy and difficult to carry. When a rookie is operating the laryngoscope for mounting the endotracheal tube, he also needs to look at the big screen while inserting the endotracheal tube into the patient's mouse. This increases the task difficulty. Thus an integrated laryngoscope that includes a lens on the front end of a blade, a light source arranged beside the lens, and a smaller screen disposed on a top side of a handle has been developed. The integrated laryngoscope is easy to use. But the viewing angle of the lens limits visibility of the screen. Once the viewing angle is a bit higher or lower, the image on the screen is not seen clearly. Thus the integrated laryngoscope is inconvenient to use.

While rescuing unconscious patients caused by drowning, hitting or other reasons, airway management is required to provide an open airway and allow the patient to breathe smoothly. If patient is vomiting or having foreign material that obstructs the airway, the patient's mouth should be opened and the larynx is observed to confirm the obstruction. If fluid or matter obstructs the airway, the head of the patient is turned slightly downwards to allow obvious foreign material (e.g. food, vomit, etc.) to drain and clear the airway.

When the patient is unconscious, the muscles are relaxed and the tongue easily falls against the back wall of the throat and blocks the larynx. Thus rescuer is difficult to see the larynx clearly. Moreover, the above observation depends on the rescuer's vision. Once the rescuer has poor vision, he is unable to get a clear view of the deeper throat. There is also a dead angle in the throat. Thus the observation mainly depends on the rescuer's techniques and experience.

In order to solve the above problem, a device used to obtain a view of the throat has been developed. The device includes a handle, and a blade. The handle allows users to hold and a power source is mounted in the handle. One end of the blade is movably connected to the handle. The patient's tongue is compressed by the blade so that the throat will not be blocked. Moreover, a light and a camera are arranged at the blade and connected to the power source. The light emits light to the patient's throat while the camera captures image of the patient's throat and transmits the images to a display by a transmission line. Thus users can directly see the patient's throat by the display and the device is more convenient to use.

Although the above device is much more convenient for users to observe the patient's throat, the wires of the power source and transmission line for image transmission increase the weight and complexity of the device. Moreover, the display is unable to be adjusted according to rescuer's needs or the position the patient is lying. This causes inconvenience to rescuers.

SUMMARY OF THE INVENTION

Therefore it is a primary object of the present invention to provide a laryngoscope with a rotatable and turnable display in which a bump of a rotating portion of a rotating assembly is locked into a slot by a plurality of elastic bodies while being rotated a specific angle and a turnover portion of a turnover assembly is fixed by a fixing member against a fixing hole of the turnover portion while being flipped a specific angle. Thus the display is rotated around the rotating assembly and is flipped around the turnover assembly. The display is convenient to use.

It is another object of the present invention to provide a laryngoscope with a rotatable and turnable display in which a bump of a rotating portion of a rotating assembly is locked into a slot by a first magnetic part and a second magnetic part while being rotated a specific angle and a turnover portion of a turnover assembly is fixed by a fixing member against a fixing hole of the turnover portion while being flipped a specific angle. Thus the display is rotated around the rotating assembly and is flipped around the turnover assembly. The display is convenient to use.

It is a further object of the present invention to provide a laryngoscope with a rotatable and turnable display in which a first stopper and a second stopper are used to prevent liquid from flowing into the laryngoscope body for water-proofing. The first stopper is located outside the second stopper, and a part of surface area of the first stopper is overlapped with a part of surface area of the second stopper.

In order to achieve the above objects, a laryngoscope with a rotatable and turnable display according to the present invention includes a laryngoscope body, a rotating assembly, a turnover assembly and a display. The laryngoscope body is used to capture an image. The rotating assembly is set on a top of the laryngoscope body and including a rotating portion, a first fixed shaft and a plurality of elastic bodies. The first fixed shaft is fixed on the top of the laryngoscope body while a rail is arranged around the first fixed shaft and at least one slot is disposed beside the rail. The rotating portion is fitted on the first fixed shaft. A bump arranged at an inner surface of the rotating portion is mounted and slid in the rail for driving the rotating portion to rotate. One side of the elastic body is fixed on an inner surface of the rotating portion while the other side thereof is against a top part of the laryngoscope body. The elastic bodies also drive the bump to be locked in the slot while the bump being rotated to the slot. The turnover assembly is composed of a second fixed shaft, a turnover portion and a fixing member. The second fixed shaft is fixed on a lateral side of the rotating portion. The turnover portion is having a plurality of fixing holes and one end of the turnover portion is fitted on the second fixed shaft while the other end thereof is fixed on one side of the display. The fixing member is mounted into a lateral side of the second fixed shaft and against the fixing hole. Thus the display that can be rotated around the rotating assembly and flipped around the turnover assembly is more convenient to use.

Furthermore, a laryngoscope with a rotatable and turnable display according to the present invention includes a laryngoscope body, a rotating assembly, a turnover assembly and a display. The laryngoscope body is used to capture an image. The rotating assembly is set on a top of the laryngoscope body and including a rotating portion, a first fixed shaft a first magnetic part and a second magnetic part. The first fixed shaft is fixed on the top of the laryngoscope body while a rail is arranged around the first fixed shaft and at least one slot is disposed beside the rail. The rotating portion is fitted on the first fixed shaft. A bump arranged at an inner surface of the rotating portion is mounted and slid in the rail for driving the rotating portion to rotate. The first magnetic part is a hollow part, fitted on the first fixed shaft and located on the bottom of the rotating portion. The second magnetic part is a hollow part, fitted on the first fixed shaft, arranged at the bottom of the rotating portion and corresponding to the first magnetic part. The first magnetic part and the second magnetic part repel each other so that bump is driven to be locked in the slot while being rotated to the slot. The turnover assembly consists of a second fixed shaft, a turnover portion and a fixing member. The second fixed shaft is fixed on a lateral side of the rotating portion. The turnover portion is having a plurality of fixing holes and one end of the turnover portion is fitted on the second fixed shaft while the other end thereof is fixed on one side of the display. The fixing member is mounted into a lateral side of the second fixed shaft and against the fixing hole. Thus the display is rotated around the rotating assembly and is flipped around the turnover assembly. Moreover, the bump of the rotating portion of the rotating assembly is locked into the slot by the first magnetic part and the second magnetic part while being rotated a specific angle and the turnover portion of the turnover assembly is fixed by a fixing member against a fixing hole of the turnover portion while being flipped a specific angle. Thus the display is rotated around the rotating assembly and is flipped around the turnover assembly. Therefore the display is more convenient to use.

In addition, the laryngoscope with a rotatable and turnable display according to the present invention further includes a first stopper and a second stopper. The first stopper is circularly disposed under the rotating portion of the rotating assembly while the second stopper is circularly arranged at a top of the laryngoscope body and located around the first fixed shaft. The first stopper is located outside the second stopper and a part of surface area of the first stopper is overlapped with a part of surface area of the second stopper so as to prevent liquid from flowing into the laryngoscope body and achieve waterproof effect.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

In the specifications and subsequent claims, certain words are used for representing specific devices. A person having ordinary skill in the art should know that hardware manufacturers might use different nouns to call the same device. In the specifications and subsequent claims, the differences in names are not used for distinguishing devices. Instead, the differences in functions are the guidelines for distinguishing. In the whole specifications and subsequent claims, the word "comprising" is an open language and should be explained as "comprising but not limited to". Beside, the word "couple" includes any direct and indirect electrical connection. Thereby, if the description is that a first device is coupled to a second device, it means that the first device is connected electrically to the second device directly, or the first device is connected electrically to the second device via other device or connecting means indirectly.

In order to learn structural features and functions of the present invention, please refer to the following embodiment and the detailed descriptions.

Figure 1:
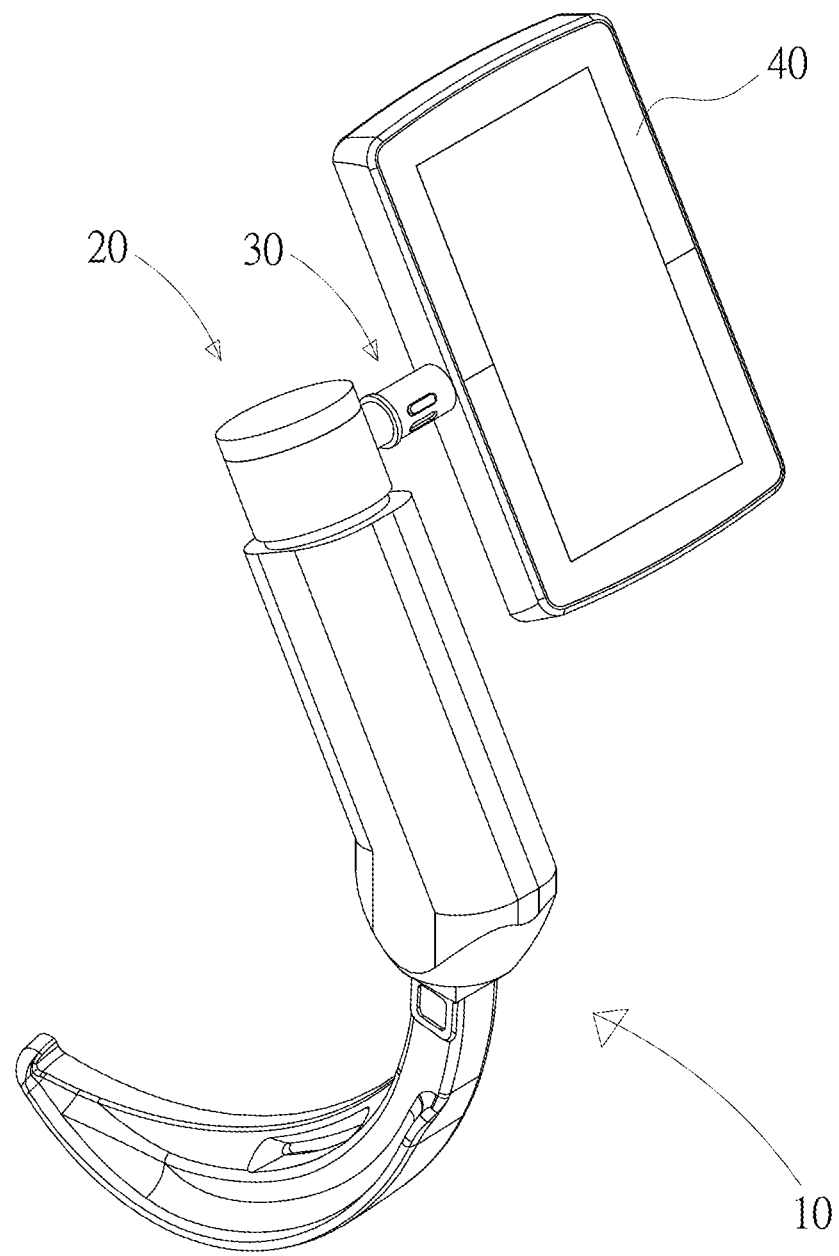
FIG. 1 is a perspective view of an embodiment according to the present invention.
Figure 2:
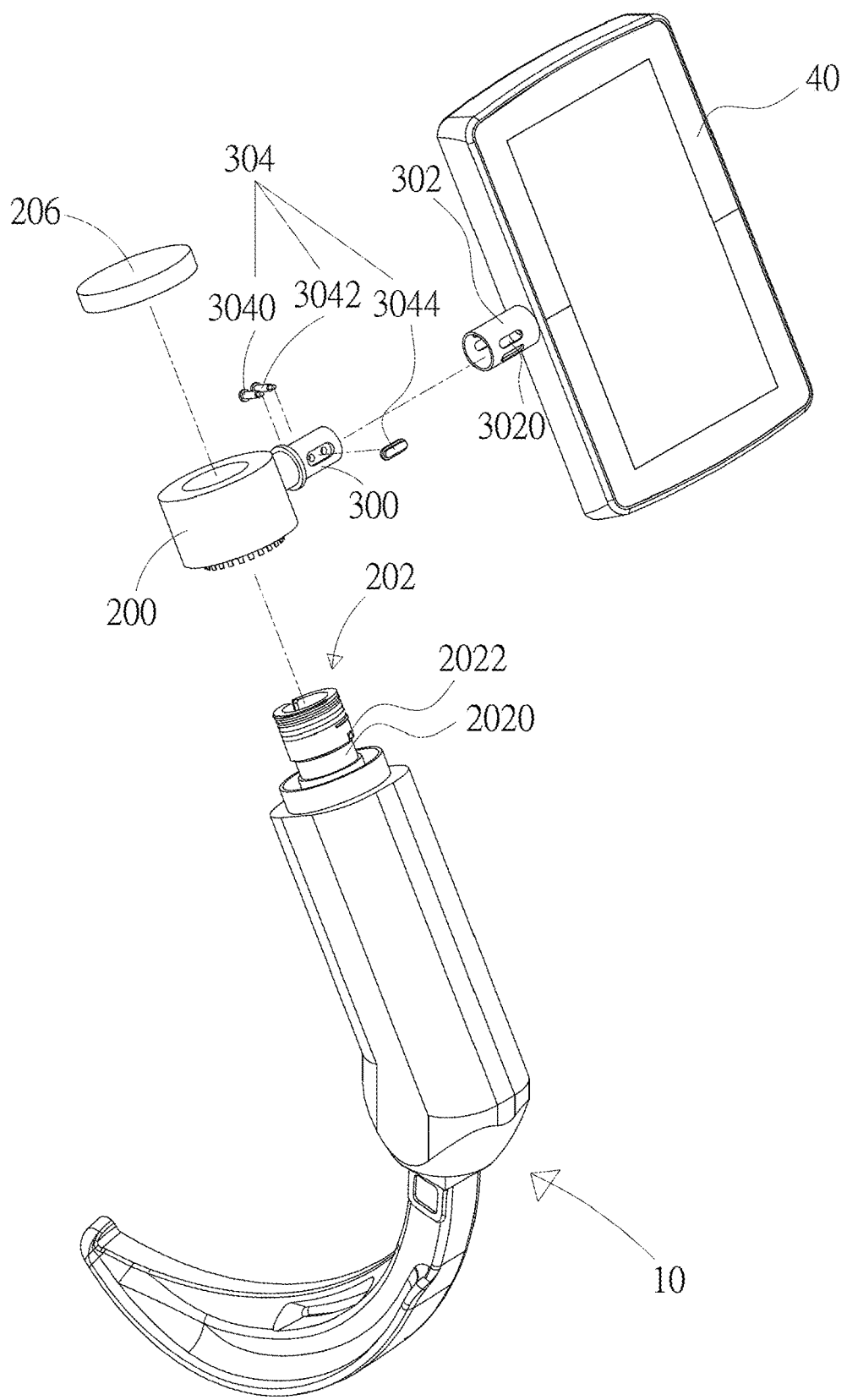
FIG. 2 is an explosive view of an embodiment according to the present invention.

Refer to FIG. 1 and FIG. 2, an embodiment of a laryngoscope with a rotatable and turnable display is revealed. The laryngoscope with a rotatable and turnable display according to the present invention includes a laryngoscope body 10, a rotating assembly 20, a turnover assembly 30 and a display 40. The laryngoscope body 10 is used to capture an image. The rotating assembly 20 is disposed on a top of the laryngoscope body 10 and including a rotating portion 200, a first fixed shaft 202 and a plurality of elastic bodies 204. The first fixed shaft 202 is fixed on the top of the laryngoscope body 10 while a rail 2020 is disposed around the first fixed shaft 202 and at least one slot 2022 is set beside the rail 2020. The rotating portion 200 is fitted on the first fixed shaft 202. A bump 2000 arranged at an inner surface of the rotating portion 200 is mounted and slid in the rail 2020 for driving the rotating portion 200 to rotate. One side of the elastic body 204 is fixed on an inner surface of the rotating portion 200 while the other side thereof is against a top part of the laryngoscope body 10 when the rotating portion 200 is fitted on the first fixed shaft 202. The elastic bodies 204 also drive the bump 2000 to be locked in the slot 2022 while the bump 2000 being rotated to the slot 2022.

The turnover assembly 30 is composed of a second fixed shaft 300, a turnover portion 302 and a fixing member 304. The second fixed shaft 30 is fixed on a lateral side of the rotating portion 200. The turnover portion 302 is having a plurality of fixing holes 3020 and one end of the turnover portion 302 is fitted on the second fixed shaft 300 while the other end thereof is fixed on one side of the display 40. The fixing member 304 is mounted into a lateral side of the second fixed shaft 300 and against the fixing hole 3020. The display 40 is rotated around the rotating assembly 20 and is flipped around the turnover assembly 30. The bump 2000 in the rotating portion 200 of the rotating assembly 20 is rotated a specific angle by the elastic bodies 204 to be locked into the slot 2022. Then the turnover portion 302 of the turnover assembly 30 is flipped a specific angle and the fixing member 304 is against the fixing hole 3020 of the turnover portion 302. Thus the display 40 can be rotated around the rotating assembly 20 and flipped around the turnover assembly 30 easily. Therefore the display 40 is more convenient to use.

In order to learn how the display 40 is rotated around the rotating assembly 20 and flipped around the turnover assembly 30, please refer to the following detailed descriptions.

Figure 3:
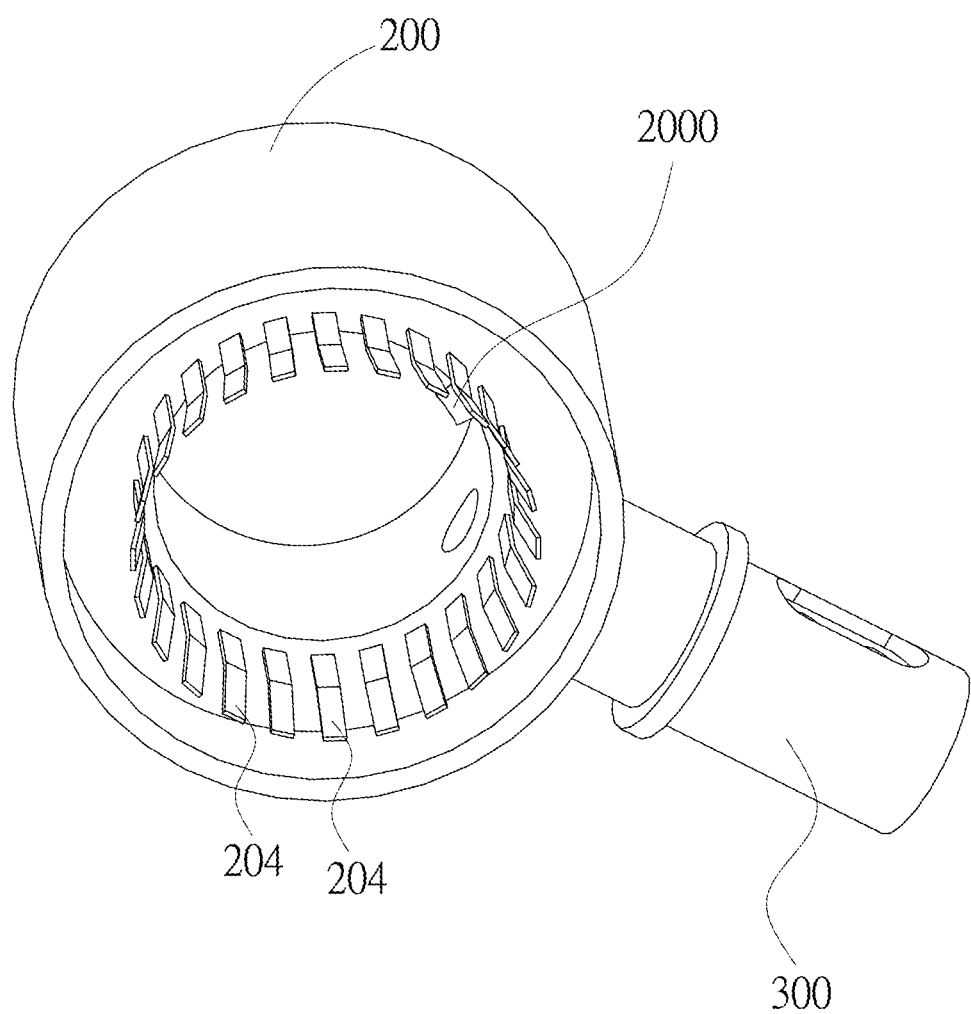
FIG. 3 is a schematic drawing showing a rotating portion of a rotating assembly of an embodiment according to the present invention.
Figure 4:
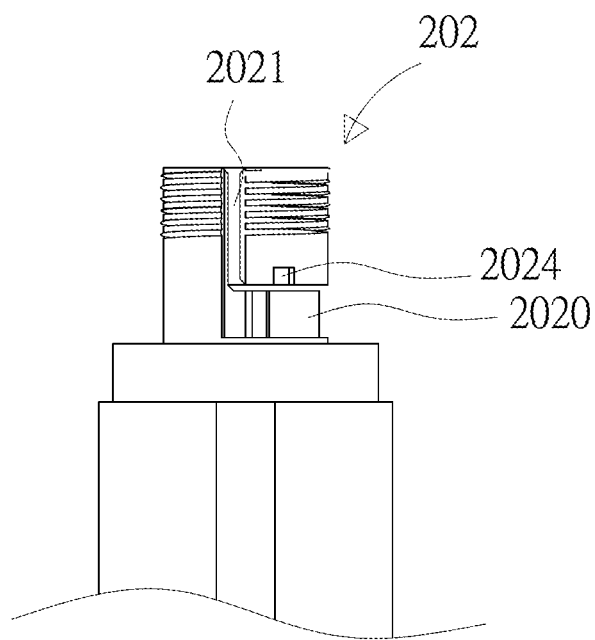
FIG. 4 is a schematic drawing showing a first slot of a first fixed shaft of rotating assembly of an embodiment according to the present invention.
Figure 5:
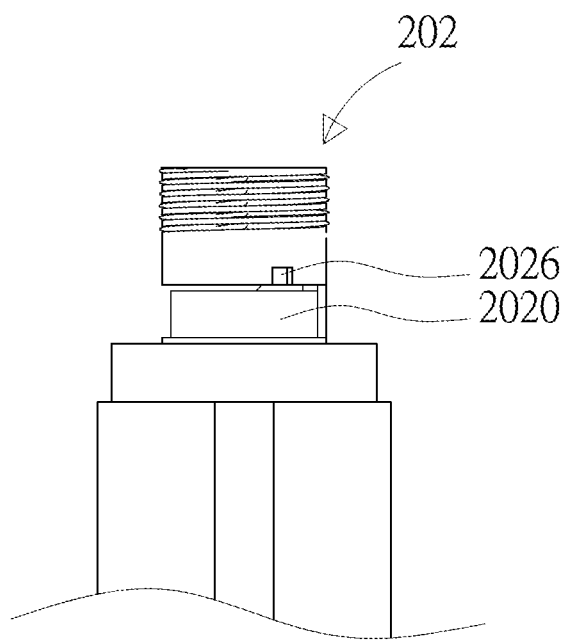
FIG. 5 is a schematic drawing showing a second slot of a first fixed shaft of rotating assembly of an embodiment according to the present invention.

Refer to FIG. 3, FIG. 4 and FIG. 5, schematic drawings showing the rotating portion 200 of the rotating assembly 20, a first slot 2024 and a second slot 2026 of the first fixed shaft 202 of the rotating assembly 20 are revealed. As shown in the figures, the rotating assembly 20 includes the rotating portion 200, the first fixed shaft 202 and the elastic bodies 204. The rotating portion 200 is a hollow cylinder corresponding to a holding part of the laryngoscope body 10 and being fit on the first fixed shaft 202. The bump 2000 is arranged at an inner surface of the rotating portion 200 while the first fixed shaft 202 is disposed with a passage 2021 and the rail 2020. The rail 2020 is circularly set on an outer wall of the first fixed shaft 202 and is connected to the passage 2021. Thus the rotating portion 200 is fitted on the first fixed shaft 202 by the bump 2000 passed through the passage 2021 and mounted in the rail 2020. Owing to the rail 2020 around the outer wall of the first fixed shaft 202, the rotating portion 200 can be rotated by the bump 2000 sliding in the rail 2020.

Moreover, at least one slot 2022 is set beside the rail 2020. One side of each elastic body 204 is fixed on an inner surface of the rotating portion 200 while the other side thereof is against a top part of the laryngoscope body 10 when the rotating portion 200 is fitted on the first fixed shaft 202. The elastic bodies 204 also drive the bump 2000 to be locked in the slot 2022 while the bump 2000 being rotated to the slot 2022. The elastic bodies 204 support the rotating portion 200 when the bump 2000 is inside the rail 2020. While the bump 2000 being rotated to the slot 2022, the elastic bodies 204 drives the bump 2000 moving and locking into the slot 2022. When users intend to rotate the display 40 again, they only need to press the rotating portion 200 to make the bump 2000 move from the slot 2022 to the rail 2020. Then the display 40 can be rotated by rotating the rotating portion 200.

Furthermore, the elastic body 204 can be curved or L-shaped for providing an upward force while the rotating portion 200 is fitted on the first fixed shaft 202. Thus the bump 2000 is driven by the upward force to move into the slot 2022 while being rotated to the slot 2022. The elastic body 204 is made from elastoplastic or silicone rubber.

The rotation angle of the laryngoscope is determined according to the position of the slot 2022. The position of the slot 2022 arranged beside the rail 2020 is designed according to the required rotation angle of the display 40. In this embodiment, the laryngoscope is disposed with a first slot 2024 and a second slot 2026, both set beside the rail 2020, located at the same side of the rail 2020 and opposite to each other. When the bump 2000 of the rotating portion 200 is moved from the first slot 2024 to the second slot 2026, the rotating portion 200 also drives the display 40 to rotate 180 degrees. Similarly, there can be four slots 2022 in other embodiment. The slots 222 are equally spaced around the first fixed shaft 202 so that the display is able to be rotated 90 degrees each time. The more slots 222 the first fixed shaft 202 is disposed, the more rotation angles of the display 40 are available.

Figure 6:
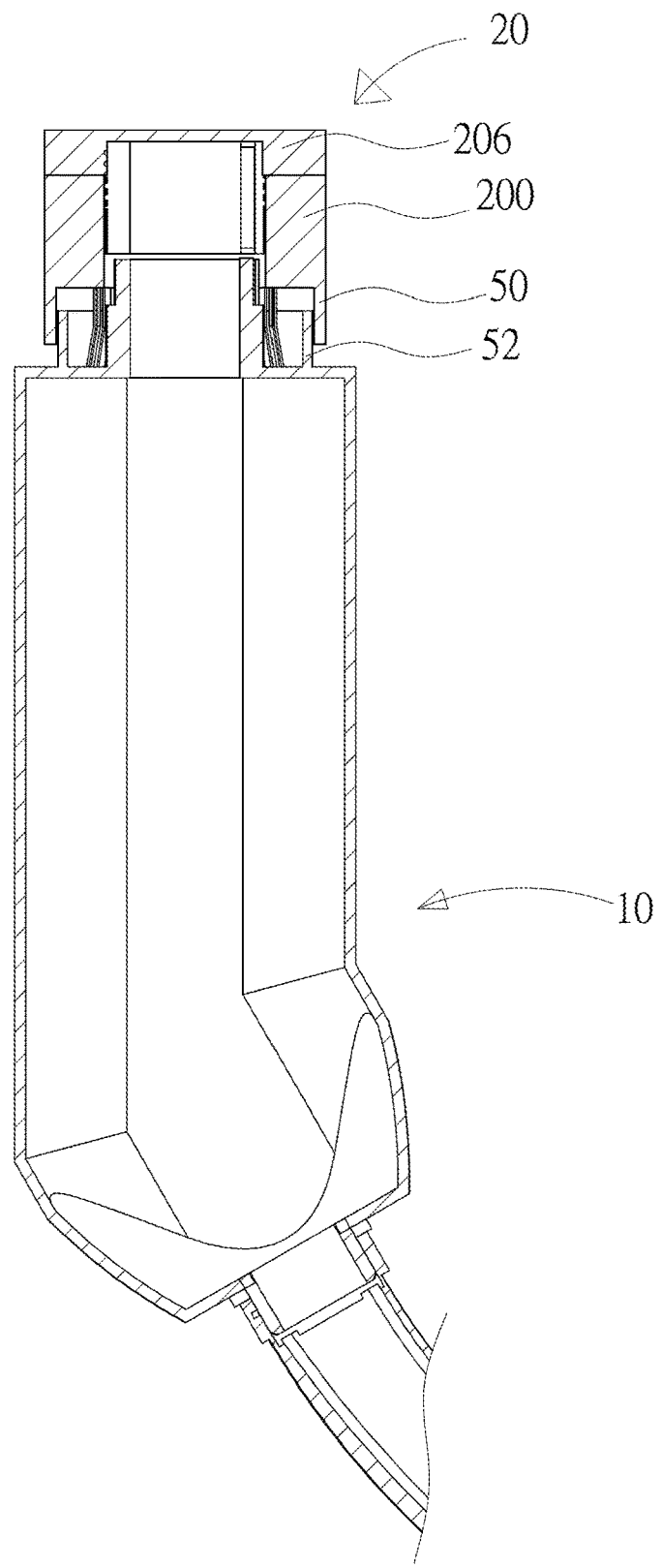
FIG. 6 is a longitudinal sectional view of a rotating assembly and a laryngoscope body of an embodiment according to the present invention.

Refer to FIG. 6, a longitudinal sectional view of the laryngoscope body 10 and the rotating assembly 20 of an embodiment is revealed. The laryngoscope with the rotatable and turnable display 40 further includes a first stopper 50 and a second stopper 52. The first stopper 50 is circularly disposed under the rotating portion 200 while the second stopper 52 is circularly arranged at a top of the laryngoscope body 10 and located around the first fixed shaft 202. The first stopper 50 is located outside the second stopper 52 while a part of surface area of the first stopper 50 and a part of surface area of the second stopper 52 are overlapped. The first and the second stoppers 50, 52 prevent liquid from flowing into the laryngoscope body 10 for water-proofing.

Moreover, the laryngoscope of the present invention further includes a top cover 206 located on top of the rotating portion 200. The top cover 206 is disposed with an inner thread corresponding to and engaged with an outer thread of the first fixed shaft 202. Thus the rotation of the rotating portion 200 around the first fixed shaft 202 is limited by the top cover 206. The top cover 206 prevents the rotating portion 200 from moving out of the first fixed shaft 202 while being rotated.

Figure 7:
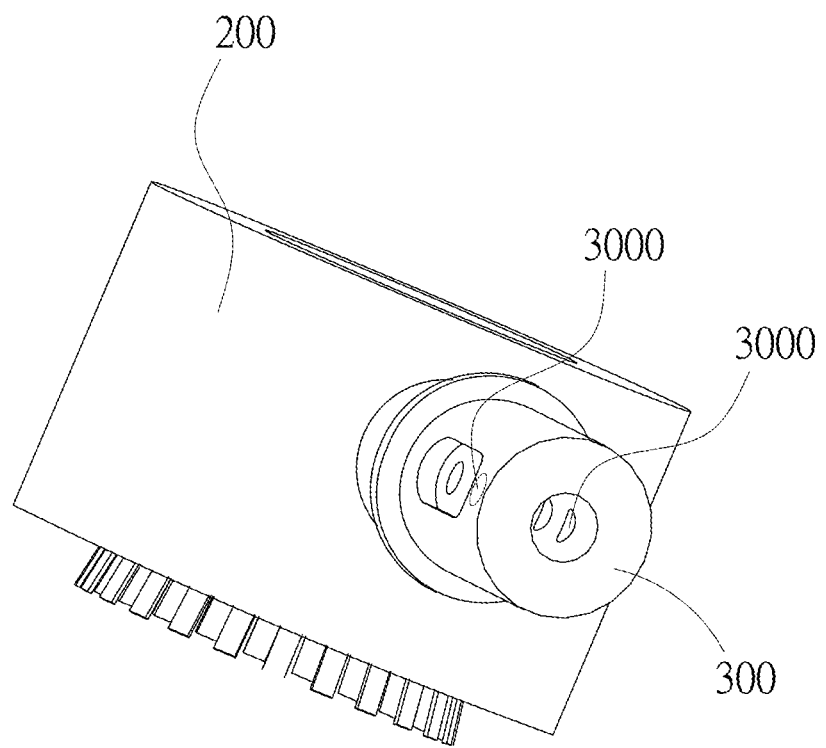
FIG. 7 is a schematic drawing showing a second fixed shaft disposed on a rotating portion of an embodiment according to the present invention.
Figure 8:
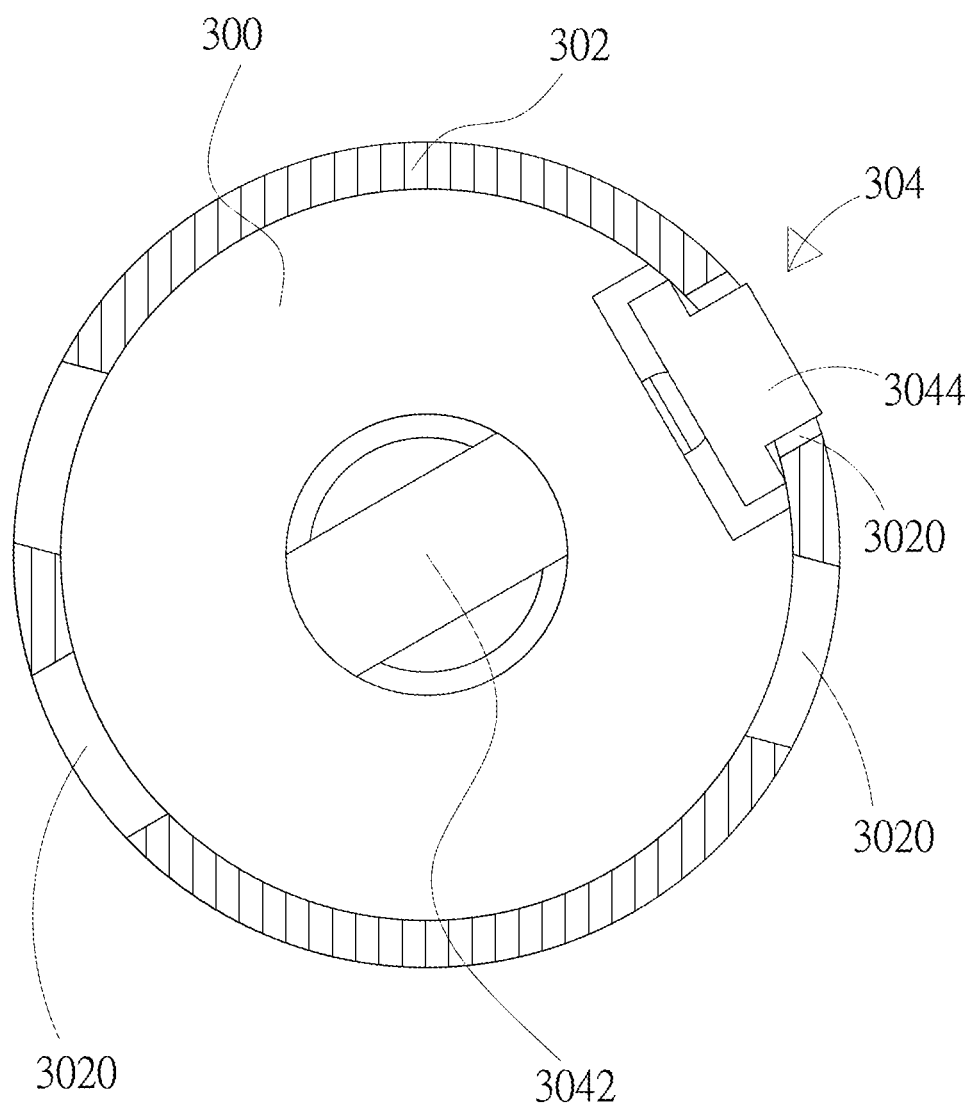
FIG. 8 is a cross sectional view of a turnover portion of an embodiment according to the present invention.

Refer to FIG. 2, FIG. 7 and FIG. 8, the turnover assembly 30 consists of the second fixed shaft 300, the turnover portion 302 and the fixing member 304. The second fixed shaft 300 is fixed on a lateral side of the turnover portion 302 (as shown in FIG. 7) and at least one insertion hole 3000 is disposed on a lateral side of the second fixed shaft 300. The turnover portion 302 including a plurality of fixing holes 3020 is fitted on the second fixed shaft 300. The fixing member 304 is passed through the insertion hole 3000 of the second fixed shaft 300 and against the fixing hole 3020 so as to fix the flip angle of the display 40. The positions of the fixing holes 3020 arranged at the turnover portion 302 are determined according to the flip angle of the display 40 users need. In this embodiment, there are two pairs of fixing holes 3020 arranged at the turnover portion 302. In each pair, the two fixing holes 3020 are disposed opposite to each other. An angle between the two adjacent fixing holes 3020. enables the display 40 to be flipped 45 degrees. Thus users can adjust the flip angle of the display 40 according to the usage now. The more fixing holes 3020 the turnover portion 302 is disposed, the more flip angles of the display 40 are available.

In this embodiment, the fixing member 304 consists of a first pogo pin 3040, a second pogo pin 3042 and a stopping part 3044. Both the first pogo pin 3040 and the second pogo pin 3042 are compressible, passed through and arranged at a lateral side of the second fixed shaft 300. The stopping part 3044 set on top of the pogo pin 3040 and the second pogo pin 3042 is fixed on the fixing hole 3020 of the turnover portion 302 according to elastic force of the pogo pin 3040 and the second pogo pin 3042. When the turnover portion 302 is flipped to the angle required by the fixing holes 3020 of the turnover portion 302, and the first pogo pin 3040, the second pogo pin 3042 and the stopping part 3044 passed through the second fixed shaft 300, the stopping part 3044 is driven by the springs inside the first and the second pogo pins 3040, 3042 to be locked in one of the fixing holes 3020. Thus the display 40 is stopped and fixed at the required angle corresponding to the position of the fixing holes 3020. Once the user wants to flip the display 40 continuously, he/she can press the stopping part 3044 to make the stopping part 3044 release from the fixing holes 3020 and the display 40 is driven to flip by the turnover portion 302.

Figure 9A:
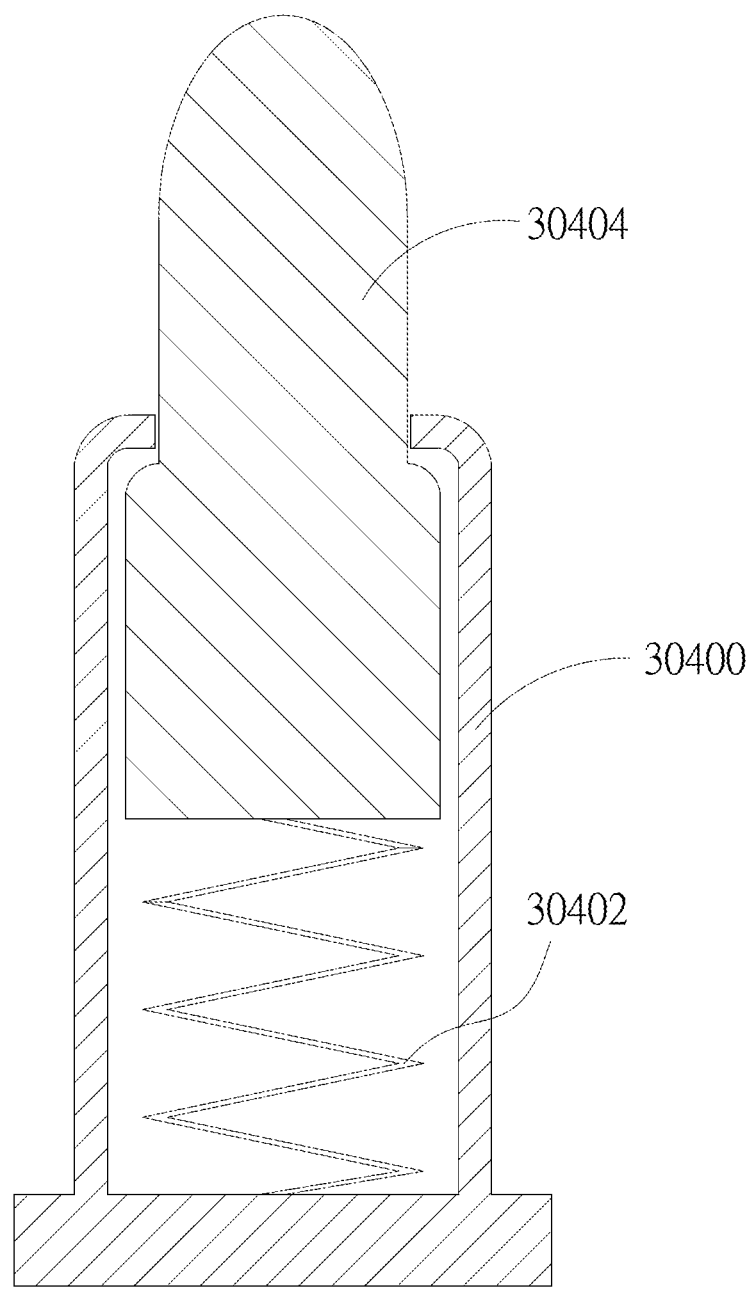
FIG. 9A is a schematic drawing showing a pogo pin in use of an embodiment according to the present invention.
Figure 9B:
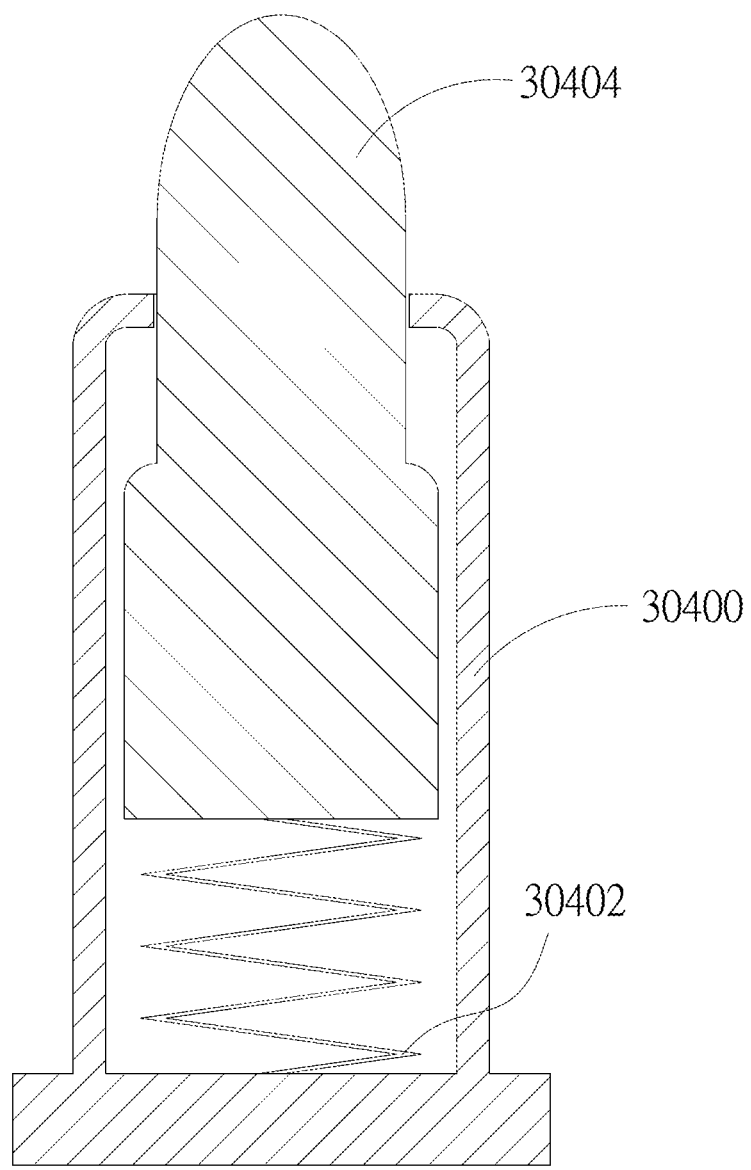
FIG. 9B is another schematic drawing showing a pogo pin in use of an embodiment according to the present invention.

Refer to FIG. 9A and FIG. 9B, schematic drawings showing a pogo pin in use of another embodiment according to the present invention are revealed. A first pogo pin 3040 and a second pogo pin 3042 of this embodiment include a tube 30400, a spring 30402, and a plunger 30404. The tube 30400 is hollow while the spring 30402 is mounted in the tube 30400 and disposed on a bottom of the tube 30400. The plunger 30404 is located in the tube 30400 and arranged at a top of the spring 30402 while a part of the plunger 30404 is exposed from an opening of the tube 30400. Thereby the plunger 30404 of the first pogo pin 3040 and the plunger 30404 of the second pogo pin 3042 are fixed on the stopping part 3044 so that the stopping part 3044 is compressible due to elastic force of the springs 30402. Thus the stopping part 3044 is driven by the springs 30402 to be locked in the fixing hole 3020 while the turnover portion 302 being flipped to the angle corresponding to the fixing hole 3020.

Figure 10:
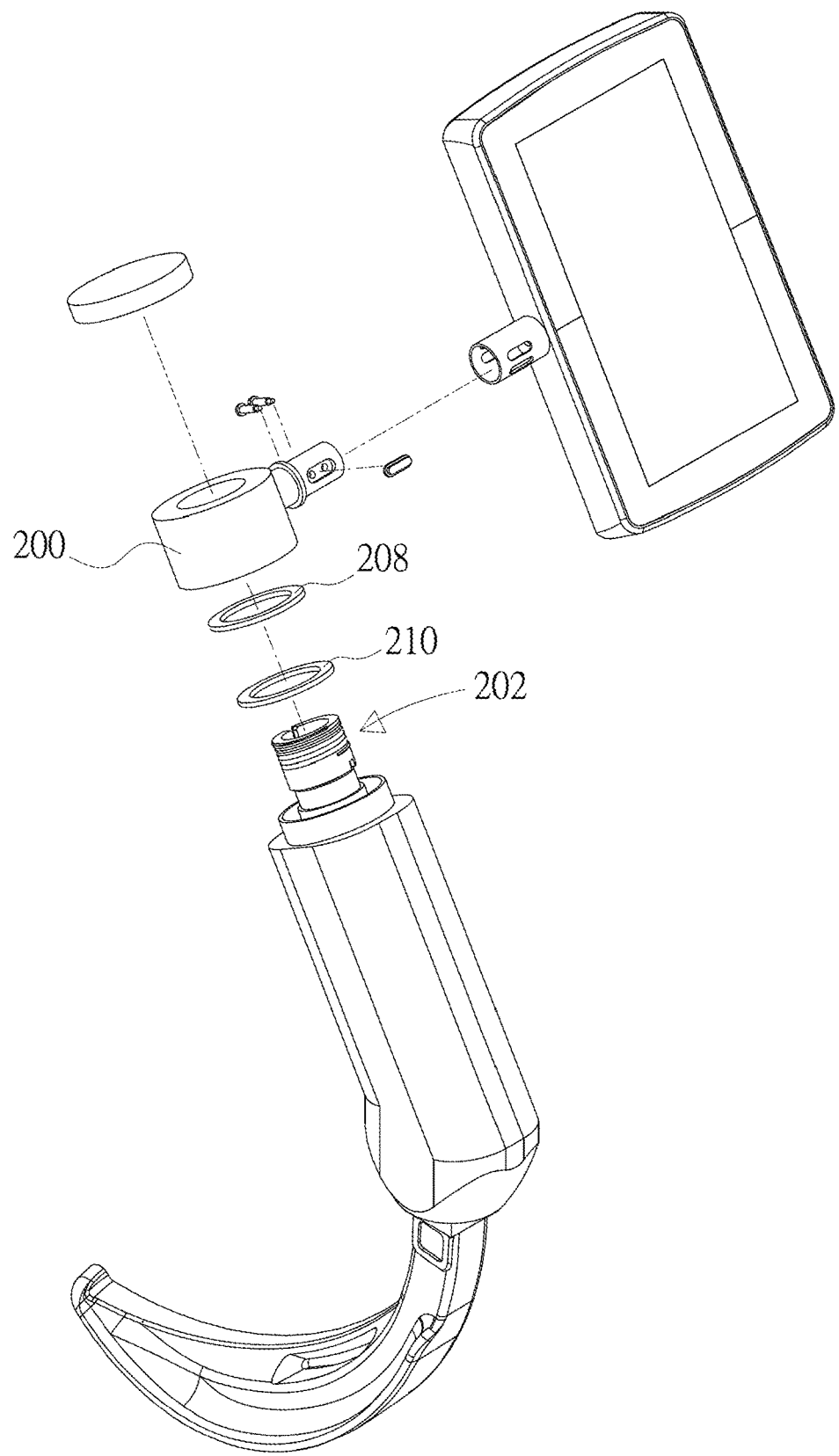
FIG. 10 is an explosive view of another embodiment according to the present invention.
Figure 11:
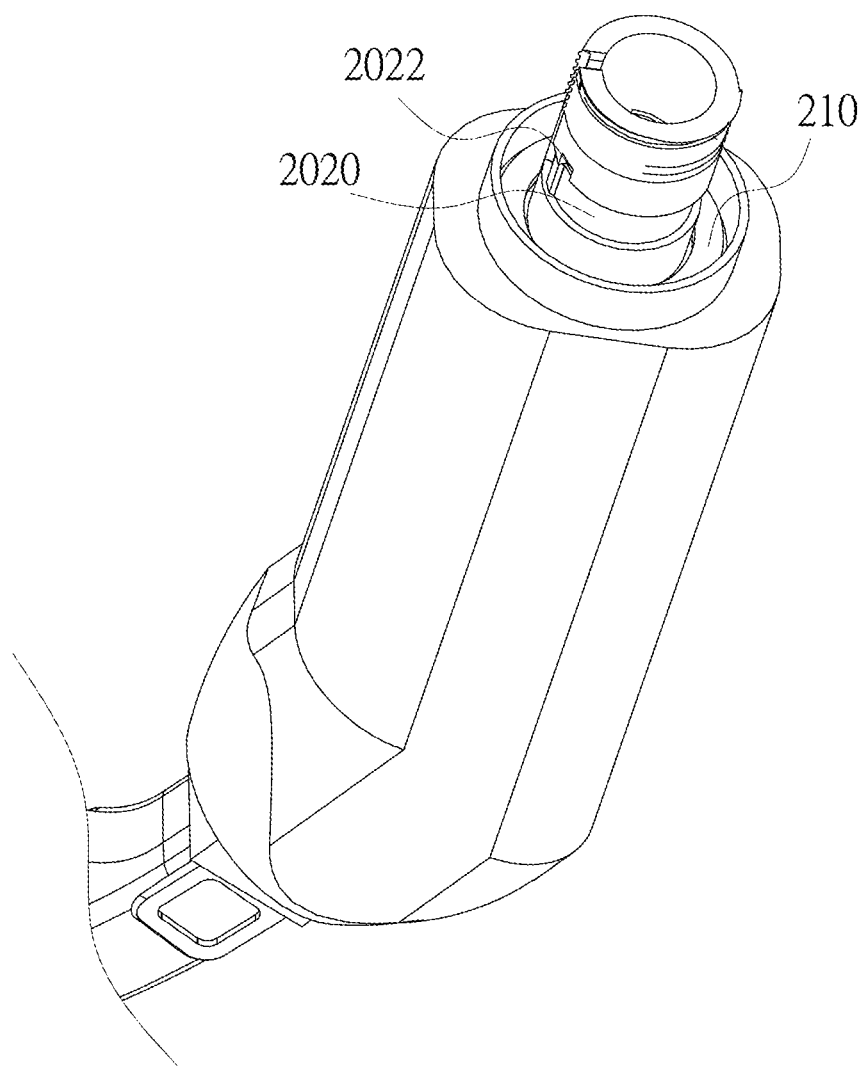
FIG. 11 is another schematic drawing showing a first fixed shaft of an embodiment according to the present invention.
Figure 12:
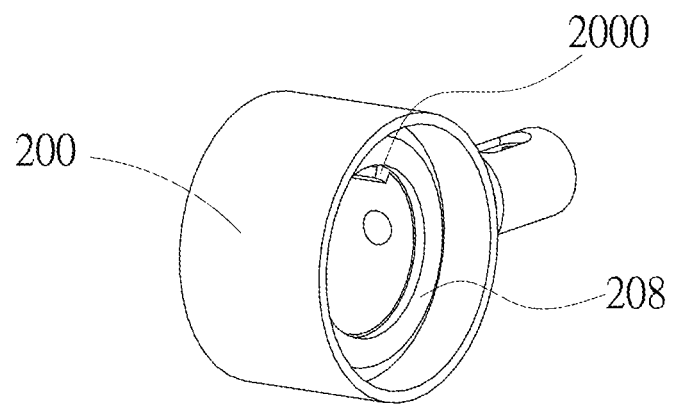
FIG. 12 is another schematic drawing showing a bottom side of a rotating portion of an embodiment according to the present invention.
Figure 13:
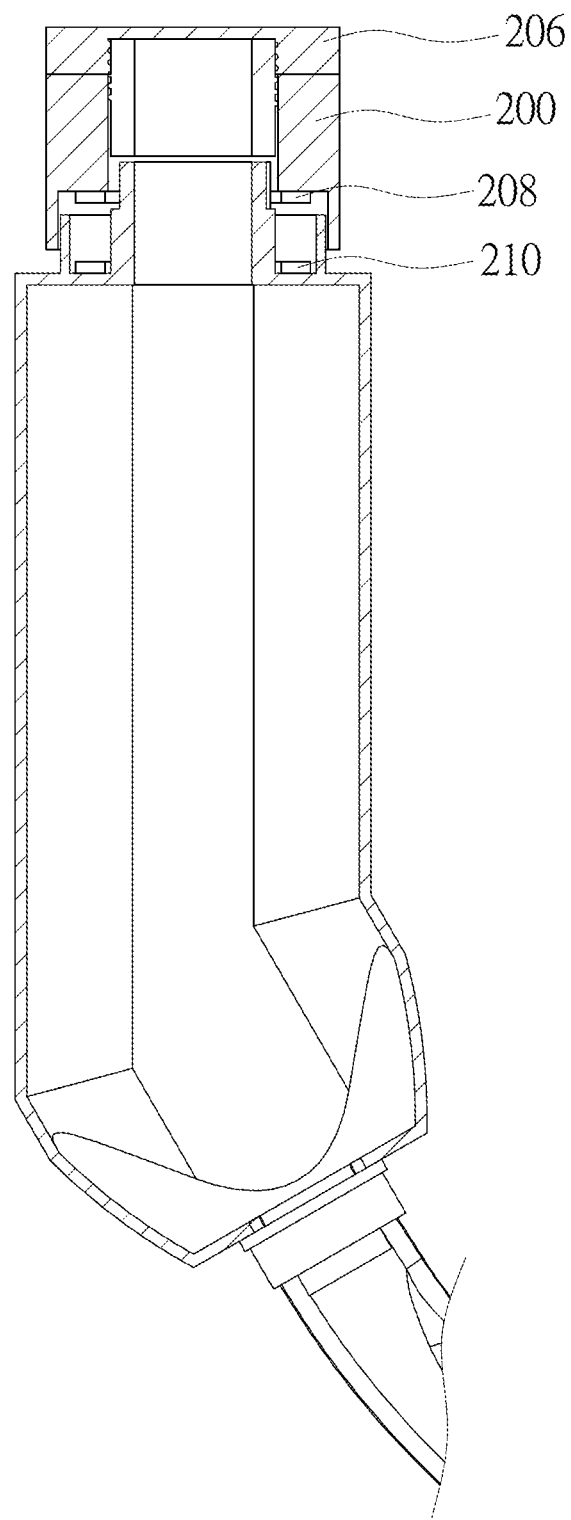
FIG. 13 is a longitudinal sectional view of a rotating assembly and a laryngoscope body of an embodiment according to the present invention.

Refer to FIG. 10 to FIG. 13, another embodiment of the present invention is disclosed. The difference between this embodiment and the above one is in that a first magnetic part 208 and a second magnetic part 210 of this embodiment are used to replace the elastic bodies 204 of the rotating assembly 20 of the above embodiment. The first magnetic part 208 is a hollow part, fitted on the first fixed shaft 202 and located on the bottom of the rotating portion 200, as shown in FIG. 12 and FIG. 13. The second magnetic part 210 is a hollow part, fitted on the first fixed shaft 202, arranged at the bottom of the rotating portion 200 and corresponding to the first magnetic part 208, as shown in FIG. 10 and FIG. 13. The first magnetic part 208 and the second magnetic part 210 repel each other so that bump 2000 is driven to be locked in the slot 2022 while being rotated to the slot 2022. Based on the principle that the magnets of the same polarity will repel each other, the rotating portion 200 provides an upward force. A repelling force of the first and the second magnetic parts 208, 210 drives the bump 2000 to be locked in the slot 2022 when the bump 2000 is rotated to the slot 2022. Once the user intends to rotate the display 40, he/she needs to press the rotating portion 200 to make the bump 2000 release from the slot 2022 and turn back to the rail 2020. Then the rotating portion 200 can be rotated again by the user for rotating the display 40. Thereby the bump 2000 of the rotating portion 200 is locked into the slot 2022 by the first and the second magnetic parts 208, 210 while being rotated a specific angle. Then the turnover portion 302 of the turnover assembly 30 is turned a specific angle and is fixed by the fixing member 304 against the fixing hole 3020 of the turnover portion 302. Therefore the display 40 can be rotated around the rotating assembly 20 and flipped around the turnover assembly 30, quite convenient to use.

Thus the present invention is new, involving an inventive step and capable of industrial applications.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A laryngoscope with a rotatable and turnable display comprising:
    a laryngoscope body used to capture an image,
    a rotating assembly set on a top of the laryngoscope body and including
        a first fixed shaft fixed on top of the laryngoscope body and having a rail arranged therearound and a slot disposed beside the rail,
        a rotating portion fitted on the first fixed shaft and having a bump arranged at an inner surface thereof and being slid in the rail for driving the rotating portion to rotate, and
        a plurality of elastic bodies each of which having one side fixed on an inner surface of the rotating portion and another side thereof against a top part of the laryngoscope body; the elastic bodies used for driving the bump to be locked in the slot while the bump is being rotated to the slot;
    a turnover assembly having
        a second fixed shaft that is fixed on a lateral side of the rotating portion;
        a turnover portion disposed with a plurality of fixing holes and having one end thereof fitted on the second fixed shaft; and
        a fixing member mounted into a lateral side of the second fixed shaft and against the fixing holes; and
    a display rotated around the rotating assembly, flipped around the turnover assembly, and having one side disposed with another end of the turnover portion of the turnover assembly.

2. The device as claimed in claim 1, wherein the elastic bodies are curved or L-shaped.

3. The device as claimed in claim 2, wherein the elastic bodies are made from elastoplastic or silicone rubber.

4. The device as claimed in claim 1, wherein the slot is disposed on the first fixed shaft according to an angle of the display to be rotated.

5. The device as claimed in claim 1, wherein the fixing holes are disposed on the turnover portion according to an angle of the display to be flipped.

6. The device as claimed in claim 1, wherein the fixing member includes:
    a first pogo pin passed through and arranged at the lateral side of the second fixed shaft;
    a second pogo pin passed through and arranged at the lateral side of the second fixed shaft; and
    a stopping part set on top of the first pogo pin and the second pogo pin; the stopping part is fixed on the fixing holes of the turnover portion according to elastic force of the first pogo pin and the second pogo pin.

7. The device as claimed in claim 6, wherein either the first pogo pin or the second pogo pin include:
    a tube that is hollow;
    a spring mounted in the tube and located on a bottom of the tube; and a plunger located in the tube, arranged at a top of the spring and having a part thereof being exposed from an opening of the tube.

8. The device as claimed in claim 1, wherein the laryngoscope further includes:
a first stopper that is circularly disposed under the rotating portion; and
a second stopper that is circularly arranged at a top of the laryngoscope body and located around the first fixed shaft;
wherein the first stopper is located outside the second stopper and a part of area of the first stopper is overlapped with a part of area of the second stopper.

9. The device as claimed in claim 1, wherein the first fixed shaft is disposed with an outer thread and the laryngoscope further includes a top cover located on top of the rotating portion and arranged with an inner thread corresponding to and engaged with the outer thread of the first fixed shaft for limiting rotation of the rotating portion around the first fixed shaft.

\* \* \* \* \*